United States Patent [19]

Greenwood et al.

[11] Patent Number: 5,856,172
[45] Date of Patent: Jan. 5, 1999

[54] PRESERVATION OF MICROORGANISMS IN A VIAL WITH A CAP COMPRISING AN IMMOBILIZED DESICCANT

[75] Inventors: Rick Greenwood, San Juan Capistrano; Nathan Greene, Newbury Park, both of Calif.

[73] Assignee: Quality Technologies, LLC, Newbury Park, Calif.

[21] Appl. No.: 778,478

[22] Filed: Jan. 3, 1997

[51] Int. Cl.$^6$ .............................. C12N 1/00; C12N 1/04
[52] U.S. Cl. ...................... 435/260; 435/243; 435/307.1; 435/810
[58] Field of Search ..................................... 435/243, 260, 435/307.1, 810

[56] References Cited

U.S. PATENT DOCUMENTS

| | | | |
|---|---|---|---|
| 3,671,400 | 6/1972 | Cekoric, Jr. et al. | 435/34 |
| 3,843,456 | 10/1974 | Haden et al. | 435/287.7 |
| 4,217,419 | 8/1980 | Suzuki | 435/252.9 |
| 4,246,349 | 1/1981 | Messing et al. | 435/176 |
| 4,672,037 | 6/1987 | Daggett et al. | 435/252.1 |
| 4,800,156 | 1/1989 | Yuhda | 435/303.2 |
| 4,956,295 | 9/1990 | Sudoma | 435/252.1 |
| 5,155,039 | 10/1992 | Chrisope et al. | 435/243 |
| 5,279,964 | 1/1994 | Chrisope | 435/307.1 |
| 5,543,115 | 8/1996 | Karakawa | 422/102 |

OTHER PUBLICATIONS

K.A. Malik, "Maintenance of Microorganisms by Simple Methods," in *Maintenance of Microorganisms*, 2d ed., B.E. Kirsop and A. Doyle (eds.), Academic Press, London, (1991), pp. 121–132.

J.J.S. Snell, "General Introduction to Maintenance Methods," in *Maintenance of Microorganisms*, 2d ed., B.E. Kirsop and A. Doyle (eds.), Academic Press, London, (1991), pp. 21–30.

E.R. James, "Maintenance of Parasitic Protozoa by Cryopreservation," in *Maintenance of Microorganisms*, 2d ed., B.E. Kirsop and A. Doyle (eds.), Academic Press, London, (1991), pp. 209–226.

P.H. Calcott and A.M. Gargett, "Mutagenicity of Freezing and Thawing," FEMS Microbiol. Lett., 10:151–155 (1981).

D.L. Williams and P.H. Calcott, "Role of DNA Repair Genes and an R Plasmid in Conferring Cryoresistance on *Pseudomonas aeruginosa*," J. Gen. Microbiol., 128:215–218 (1982).

B.E. Kirsop, "Maintenance of Yeasts," in *Maintenance of Microorganisms*, 2d ed., B.E. Kirsop and A. Doyle (eds.), Academic Press, London, (1991), pp. 161–182.

R.K.A. Feltham et al., "A Simple Method of Storage of Bacteria at –76°C," J. Appl. Bacteriol., 44:313–316 (1978).

Jones et al., "Maintenance of Bacteria on Glass Beads at –60°C to –76°C," in *Maintenance of Microorganisms*, 2d ed., B.E. Kirsop and A. Doyle (eds.), Academic Press, London, (1991), pp. 45–50.

T.M. Sidyakina, "Low Temperature Freezing of Microorganisms on Silica Gel," in *Maintenance of Microorganisms*, 2d ed., B.E. Kirsop and A. Doyle (eds.), Academic Press, London, (1991), pp. 65–70; and.

R.H. Rudge, "Maintenance of Bacteria by Freeze–Drying," in *Maintenance of Microorganisms*, 2d ed., B.E. Kirsop and A. Doyle (eds.), Academic Press, London, (1991), pp. 31–44.

H.T. Meryman, "*Cryoprotective Agents,*" Cryobiol., 8:173–183 (1971).

(List continued on next page.)

*Primary Examiner*—Leon B. Lankford, Jr.
*Assistant Examiner*—Christopher R. Tate
*Attorney, Agent, or Firm*—Medlen & Carroll, LLP

[57] ABSTRACT

The present invention provides methods and compositions for the safe, effective, and efficient storage and transport of microbial cultures. In particular, the present invention provides compositions and methods for the storage and transport of bacterial cultures. The present invention is suitable for use in circumstances where long-term storage of microbial cultures is desired.

11 Claims, 2 Drawing Sheets

OTHER PUBLICATIONS

E.B. Seligmann and J.F. Farber, "Freeze Drying and Residual Moisture," Cryobiol., 8:138–144 (1971).

R.J. Heckley, "Principles of Preserving Bacteria by Freeze–Drying," Develop. Indust. Microbiol., 26:379–395 (1985).

J.M. Barabee et al., "Problems in Freeze–Drying: I. Stability in Glass–Sealed and Rubber–Stoppered Vials," Develop. Indust. Microbiol., 26:397–405 (1985).

J.M. Barabee et al., "Problems in Freeze–Drying: II. Cross–Contamination During Lyophilization," Develop. Indust. Microbiol., 26:407–409 (1985).

J.M. Barabee and A. Sanchez, "Cross–Contamination During Lyophilization," Cryobiol., 19:443–447 (1982).

PRESERVATION OF MICROORGANISMS IN A VIAL WITH A CAP COMPRISING AN IMMOBILIZED DESICCANT

FIELD OF THE INVENTION

The present invention relates to methods and compositions for preservation of microorganisms. In particular, the present invention provides methods and compositions for the safe storage and transport of preserved bacteria.

BACKGROUND OF THE INVENTION

Over the years, microbiologists have developed various methods for the storage or preservation of microorganisms, including subculturing, drying, freezing-drying, and freezing. Other methods, such as storage under liquid paraffin, in distilled water, and liquid drying (i.e., L-drying), have also been used with mixed success (See, e.g., K. A. Malik, "Maintenance of Microorganisms by Simple Methods," in *Maintenance of Microorganisms*, 2d ed., B. E. Kirsop and A. Doyle (eds.), Academic Press, London, [1991], pp. 121–132). However, no one method fulfills all of the needs of each culture; the choice of method is often the result of weighing the advantages and disadvantages of multiple methods (See e.g., J. J. S. Snell, "General Introduction to Maintenance Methods," in *Maintenance of Microorganisms*, 2d ed., B. E. Kirsop and A. Doyle (eds.), Academic Press, London, [1991], pp. 21–30).

Subculturing

Subculturing involves the periodic transfer of organisms to fresh growth media. This new culture (i.e., subculture) is allowed to grow under the appropriate conditions, its growth is slowed by refrigeration or other means, and it is used to replace the old culture. The time that is allowed to elapse between production of each subculture primarily depends upon the organism to be preserved. For example, subcultures of some organisms will remain viable for several years (e.g., some Staphylococcus cultures), while others require subculturing after only a few weeks or days (e.g., Neisseria). Although subculturing is attractive in some respects, there are many drawbacks to the method. For example, contamination presents a major problem that is present at each subculturing step. Contamination presents significant problems, as for most uses of preserved cultures, it is highly desired that the culture be pure. If a preserved culture becomes contaminated, there is the risk that the contaminants will outgrow and/or kill the original culture. Furthermore, even if there are viable organisms of interest in the contaminated culture, it may be very difficult to separate them from the contaminants. Thus, a contaminated culture is of questionable value, and it is critical to constantly monitor the purity of subcultures during the subculturing process, for the life of the culture.

In addition to the dangers of contamination, loss of viability is a constant concern. Problems with the preservation media (e.g., use of an inappropriate medium for the culture to be preserved), and dehydration of the cultures must be avoided. Storage of organisms in water, layering oil on top of the grown culture, use of media with limited nutrients and minimal carbohydrates, and for most organisms, lowering the storage temperature, may be helpful.

Furthermore, cultures preserved by continuous subculturing are very prone to genetic changes and selection. This risk increases with each subculture. Use of large inocula may help to reduce the risk, but it may increase the risk of contamination. In sum, subculturing is often convenient in situations where it is often necessary to use the culture, as it avoids the necessity of continually freezing and thawing frozen cultures or utilizing the entire lyophilized culture, if the culture has been freeze-dried. However, it is important that the culture be checked for purity before its use.

Drying

Desiccation has been widely used as a method to preserve microorganisms. A variety of methods are used, although all depend upon the removal of water from the culture and prevention of rehydration. Although drying methods have been more commonly used with molds than bacteria, some bacteria and yeasts have been successfully preserved using these methods. In the most commonly used methods, the cultures are dried in soil, sand, kieselguhr, and silica gel, dried onto paper or gelatin strips or discs, or pre-dried plugs.

None of the drying methods has found universal acceptance, as their efficacy appears to be culture-specific (i.e., some organisms may not be dried as they become non-viable during the process). For cultures that are suited for preservation by drying, long-term viability is often good, contamination is less likely than with subculturing, and capital equipment costs are small. However, stability of strain characteristics appears to be strain-specific and genetic changes have been reported.

Freezing

In freezing, water is made unavailable to the organisms, and the dehydrated cells are maintained at low temperatures. Damage may be caused to the cells during the cooling stage and/or the subsequent thawing. This damage may be caused either by the concentration of electrolytes through removal of water as ice, or by the formation of ice crystals that shear the cells. Damage may be somewhat limited by adjusting the cooling and warming rates, as well as by adding cryoprotectants (e.g., dimethyl sulfoxide (DMSO), glycerol, or blood) to the cell suspension. Although various temperatures have been used to store frozen cultures (e.g., $-20°$, $-30°$, $-40°$, $-70°$, $-140°$, and $-196°$ C.), poor results are usually observed at temperatures above $-30°$ C.

Freezing in liquid nitrogen has been widely used for many organisms (e.g., bacteria, fungi, protozoa, etc.), and is currently recommended for storage of valuable seed stock cultures. There are numerous advantages to this method, as virtually no loss of viability occurs during storage (although some cells may die during the cooling and warming); in general, there is no genetic change or loss of characters; and the longevity and stability is greater for most cultures than that obtainable by freeze-drying (See, E. R. James, "Maintenance of Parasitic Protozoa by Cryopreservation," in *Maintenance of Microorganisms*, 2d ed., B. E. Kirsop and A. Doyle (eds.), Academic Press, London, [1991], pp. 209–226; P. H. Calcott and A. M. Gargett, FEMS Microbiol. Lett., 10:151–155 [1981]; D. L. Williams and P. H. Calcott, J. Gen. Microbiol., 128:215–218 [1982]; and B. E. Kirsop, "Maintenance of Yeasts," in *Maintenance of Microorganisms*, 2d ed., B. E. Kirsop and A. Doyle (eds.), Academic Press, London, [1991], pp. 161–182).

Disadvantages of freezing cultures in liquid nitrogen include the need to continually replenish the liquid nitrogen, the high cost of equipment, the risk of explosion if glass containers are used, storage space may become problematic, and the method is not very convenient for distribution of large numbers of cultures.

A relatively recently described method for freezing and storing cultures on beads has been successful (See, R. K. A. Feltham et al., J. Appl. Bacteriol., 44:313–316 [1978]; and Jones et al., "Maintenance of Bacteria on Glass Beads at $-60°$ C. to $-76°$ C.," in *Maintenance of Microorganisms*, 2d ed., B. E. Kirsop and A. Doyle (eds.), Academic Press, London, [1991], pp. 45–50). This method is very quick, easy to perform, requires minimal storage space, and requires no manipulation during storage. The main disadvantages are related to the costs of the freezer, as well as the equipment necessary to monitor and maintain the low temperature of the cultures.

In addition, methods have been developed to preserve various microorganisms by deep freezing and cryopreservation, in which the cells are pre-dried onto desiccated carriers such as silica gel, glass beads, polymeric materials, filter paper strips, other materials (See, T. M. Sidyakina, "Low Temperature Freezing of Microorganisms on Silica Gel," in Maintenance of Microorganisms, 2d ed., B. E. Kirsop and A. Doyle (eds.), Academic Press, London, [1991], pp. 65–70; and K. A. Malik, "Maintenance of Microorganisms by Simple Methods," in Maintenance of Microorganisms, 2d ed., B. E. Kirsop and A. Doyle (eds.), Academic Press, London, [1991], pp. 121–132). Cells that have been immobilized have been reported to retain their viability and characteristics much better than free cells (See, Sidyakina supra). However, these methods require additional manipulation during the process, and may be too cumbersome for some situations.

Freeze-Drying (Lyophilization)

Freeze-drying involves the removal of water by sublimination from a frozen culture. Organisms are grown on a suitable growth medium, aliquots are suspended in an appropriate freeze-drying liquid in ampules or vials, and placed in the freeze-drying apparatus, where they are frozen, and exposed to a vacuum. The water vapor from the culture is either trapped in a refrigerated condenser unit, or in phosphorous pentoxide. After freeze-drying, the cultures are sealed in their vials, often under vacuum or in an inert gas, and are stored at room temperature, refrigerated, or frozen. Two methods of freeze-drying are commonly used in industry, namely centrifugal and shelf freeze-drying (See, R. H. Rudge, "Maintenance of Bacteria by Freeze-Drying," in Maintenance of Microorganisms, 2d ed., B. E. Kirsop and A. Doyle (eds.), Academic Press, London, [1991], pp. 31–44).

Although freeze drying has been widely used to preserve various organisms, there are problems associated with this method. For example, glass ampules are generally sealed closed with a flame (e.g., a torch), requiring some care in order to avoid injury to the operator, and some ampules are very difficult to open, requiring filing in order to sufficiently weaken the glass so that the ampule can be broken. This presents risks of contamination of the culture through the introduction of contaminants through the filed area of the ampule, as well as risk of injury to the operator, should the ampule unexpectedly break. In addition, there is the risk of injury and inoculation from the broken glass (i.e., the operator may be cut on the edge of the broken glass and be inoculated with the organisms present in the ampule). Thus, there are major safety considerations associated with the use of freeze drying methods.

Despite the number of methods available for preservation of microorganisms, it is clear that improved methods are needed. Improved methods and devices should be economical, easy and safe to use and transport, and provide for long-term viability of preserved cultures.

SUMMARY OF THE INVENTION

The present invention provides improved methods and compositions for the storage and transport of microbiological cultures. In particular, the present invention avoids the hazards associated with the use of glass ampules and vials, while providing preserved cultures with long shelf lives. In addition, the present invention provides devices for the effective preservation of lyophilized cultures.

In one embodiment, the present invention provides a container comprising a vial and a cap, wherein the cap comprises immobilized desiccant and vial engaging means. While it is not intended to limit the type of vial engaging means, in one preferred embodiment, the vial engaging means comprises threads. However, it is intended that other means to engage the vial and cap will find use in the present invention. In addition, while it is not intended that vial and/or cap be limited to a particular material, in preferred embodiments the vial and/or cap are plastic. In one embodiment, the vial and/or cap are non-breakable. In a particularly preferred embodiment, lyophilized organisms are present within the vial. Thus, in this embodiment, the vial and cap are engaged and the organisms are located within the vial.

It is also contemplated that various desiccants will be used in the present invention. In one embodiment, the desiccant is selected from the group consisting of $CaCl_2$, $CaO$, $NaOH$, $MgO$, $CaSO_4$ (e.g., Drierite™), $H_2SO_4$, silica gel, $Mg(ClO_4)_2$, and $P_2O_5$. In an alternative preferred embodiment, the desiccant provides an atmosphere within the vial (i.e., when the vial and cap are engaged) that contains approximately 1–3% moisture. In a particularly preferred embodiment, the desiccant is silica gel. In an alternative preferred embodiment, lyophilized organisms are present within the vial. Thus, in this embodiment, the vial and cap are engaged and the organisms are located within the vial, and the desiccant is immobilized within the cap.

While it is not intended that the sheath be limited to any particular material, in a particularly preferred alternative embodiment, the vial and cap combination further comprises a sheath. In a particularly preferred embodiment, the sheath is plastic. In one embodiment, the sheath completely encloses the engaged vial and cap, while in alternative embodiments, the sheath only partially encloses the engaged vial and cap.

The present invention also provides methods for preserving a sample of microorganisms comprising providing lyophilization medium, viable microorganisms, a vial, and a cap, wherein the cap comprises an immobilized desiccant; exposing the viable microorganisms to the lyophilization medium to produce a lyophilization solution; dispensing the lyophilization solution into the vial; and lyophilizing the lyophilization solution to produce a preserved culture.

In an alternative embodiment, the method of the present invention comprises the step of sealing the cap to the vial to produce a vial and cap combination (i.e., an engaged vial and cap), containing the preserved culture. In this embodiment, the vial contains the preserved culture and the cap contains the immobilized desiccant. It is contemplated that various desiccants will be used in the present invention. In one embodiment, the desiccant is selected from the group consisting of $CaCl_2$, $CaO$, $NaOH$, $MgO$, $CaSO_4$ (e.g., Drierite™), $H_2SO_4$, silica gel, $Mg(ClO_4)_2$, and $P_2O_5$. In an alternative preferred embodiment, the desiccant provides an atmosphere within the vial (i.e., when the vial and cap are engaged) that contains approximately 1–3% moisture.

In a particularly preferred embodiment, the desiccant is silica gel. In an alternative preferred embodiment, lyophilized organisms are present within the vial. Thus, in this embodiment, the vial and cap are engaged and the organisms are located within the vial, and the desiccant is immobilized within the cap.

While it is not intended that the sheath be limited to any particular material, in a particularly preferred alternative embodiment, the vial and cap combination further comprises the step of encased the vial and cap within a sheath. In a particularly preferred embodiment, the sheath is plastic. In one embodiment, the sheath completely encloses the engaged vial and cap, while in alternative embodiments, the sheath only partially encloses the engaged vial and cap.

The present invention also provides lyophilization media. In one embodiment, of the methods of the present invention, the lyophilization medium comprises one or more cryoprotectants. In an alternative embodiment, the lyophilization medium comprises bovine serum albumin, sucrose, fraction V, casein peptone, soy peptone, NaCl, $K_2HPO_4$, dextrose, thioglycollate, and ascorbic acid.

In one embodiment, microorganisms are preserved using the methods of the present invention. In a preferred embodiment, the microorganisms are bacteria.

The present invention also provides methods for preserving samples of microorganisms, comprising: providing: lyophilization medium comprising one or more cryoprotectants, microorganisms, a vial, and a cap, wherein the cap comprises an immobilized desiccant; exposing the microorganisms to the lyophilization medium to produce a lyophilization solution; dispensing the lyophilization solution into the vial; exposing the lyophilization solution to freeze-drying to produce a preserved culture; sealing the cap to the vial to produce a vial and cap combination (i.e., an engaged vial and cap) containing the preserved culture; opening the vial and cap combination; and reviving the preserved microorganisms. In one embodiment, the reviving comprises adding rehydration medium to the preserved culture within the vial and cap combination.

DESCRIPTION OF THE INVENTION

The present invention provides improved methods and compositions for the storage and transport of microbiological cultures. Specifically, the present invention provides a plastic vial and cap that are particularly suited to the preservation of microorganisms. The cap of the present invention comprises an immobilized desiccant.

Early development of the present invention focused on the use of commercially available vials and standard lyophilization media and methods. These early experiments were unsuccessful in providing cultures that were easy to rehydrate and had long shelf lives. As discussed in the Examples, early work with initial cryoprotectant formulae and without the use of desiccants resulted in cultures with initially good viability. However, viability was found to greatly deteriorate within 45 days storage in a commercial laboratory refrigerator. As described in the Examples, the incorporation of the desiccant within the cap, and the use of special lyophilization media solved this problem. For added safety (i.e., to prevent leakage), and to further prevent deterioration of the preserved organisms, a plastic sheath or film may be used to seal the device. It is intended that the sheath or film be comprised of any suitable plastic material that is capable of tightly sealing the device. For example, the wraps used to enclose cigarette packages, as well as shrink wraps (e.g., a mylar shrink wrap) used for items such as computer software and foods, may find use in the present invention. It is also contemplated that the sheath may either completely surround the vial and cap device, it may surround only a portion of the vial and cap device, or it may surround only the area where the cap is threaded into the vial.

The design of the vial and cap assembly of the present invention facilitates the safe storage and transport of preserved microorganisms. In combination with the vial and cap device, the lyophilization medium in which the organisms are preserved facilitates the preservation of viable microorganisms, in a manner such that the shelf life of the preserved organisms is longer than that obtained using other methods known in the art.

Figure 1:
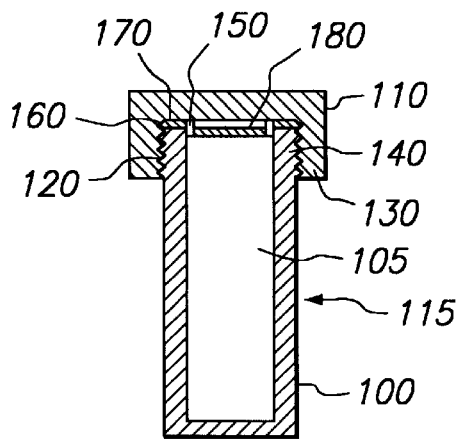
FIG. 1 is a side cross-sectional illustration of one embodiment of the vial and cap combination of the present invention.

As shown in FIG. 1, in one embodiment, the present invention provides a sealable vial (100), together with a cooperating cap (110), which may be combined to produce a vial and cap combination (115). It is preferred the cap (110) be sealingly engageable with the vial (100) by any conventional construction ("vial engaging means"). In one embodiment, the vial engaging means comprise threads. Preferably, and for safety reasons, vial (100) and cap (110) are constructed from conventional, preferably hard, plastic. However, in alternative, less preferred embodiments, any appropriate vial and cap material, such as metal, or other materials may be employed. In the preferred embodiment, vial (100) is comprised of plastic (e.g., polypropylene, polyethylene, or another polymeric material), and the interior of the vial (105) is sterile. In addition, in one embodiment, the vial (100) is provided with threads (120) about its exterior open end. It is contemplated that various vial formats will be used in the present invention. However, in one preferred embodiment, the vial is designed so that it will stand upright on a flat surface. In this embodiment, the bottom (i.e., closed end of the vial) is flat. Nonetheless, it is contemplated that round-bottomed vials will also find use in alternative embodiments of the present invention.

Figure 2:
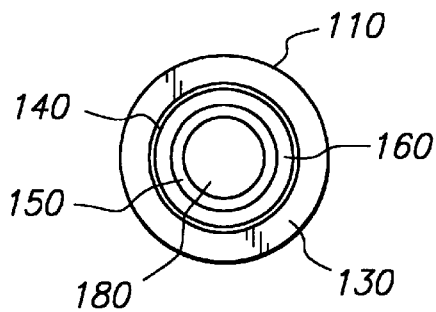
FIG. 2 is an elevation looking into the bottom of the cap of FIG. 1, illustrating the placement of the desiccant within the cap structure.

As shown in FIG. 1 and 2, in one embodiment of the cap, the underside of the cap (110) includes about its periphery, a rim (130), with interior facing threads (140) for engagement with threads of (120) of the vial (100). The underside of the cap (110) is further characterized by a protruding, circular lip (150). Lip (150), together with rim (130) define a groove (160) for receiving an elastomeric or plastic O-ring, washer, or other sealing device (170) for cooperation with the end of the vial (100) to ensure sealing engagement between the vial (100) and cap (110). Lip (150) also defines on the interior thereof, an area in which a desiccant (e.g., a desiccant tablet) (180) is immobilized.

The interior (105) of the sealed vial (100) and cap (110) combination (115) is provided with a dry biologically inert atmosphere. In some embodiments, the atmosphere is oxygen-free. However, in preferred embodiments, the atmosphere within the sealed vial and cap combination (i.e., the vial and cap have been engaged), the atmosphere within the vial contains 1–3% moisture. Controlling the atmosphere within the sealed vial aids in preservation of viable, lyophilized organisms. Those skilled in the art are aware of many methods for producing such an atmosphere, including the use of vacuum. The desiccant (180) present in the cap (110) also assists in maintaining a suitable atmosphere within the interior of the vial.

Figure 3A:
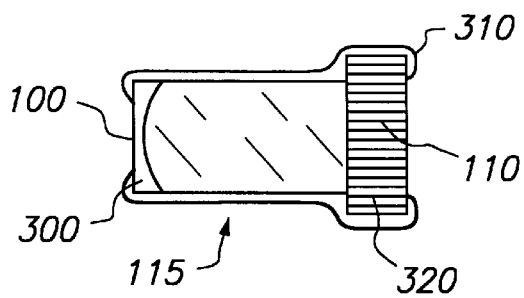
FIG. 3A is an elevational illustration showing the vial and cap combination of one embodiment of the present invention, in which dried organisms are located within the vial and the vial and cap are disposed in a sheath.
Figure 3B:
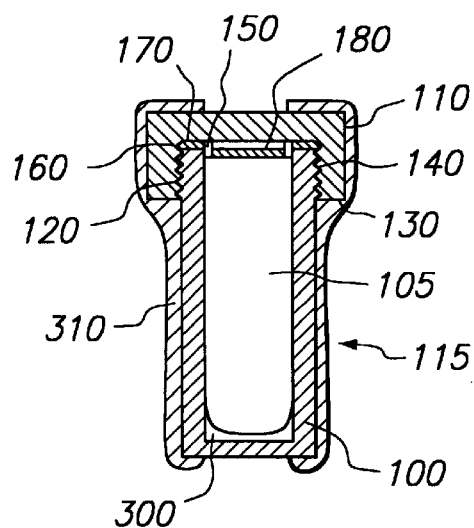
FIG. 3B is a side cross-sectional illustration of the vial and cap combination of one embodiment of the present invention, in which dried organisms are located within the vial and the vial and cap are disposed within a sheath.

In a preferred embodiment, illustrated in FIG. 3, the sealed vial (100) and cap (110) combination (115) contains a film (300) of dried organisms, is sealed within a plastic or mylar sheath (310)(i.e., the sealed vial and cap are contained within the sheath). For convenience and safety during the manipulation of the vial (100) and cap (110) combination, in preferred embodiments, the exterior of the vial is striated, such that it is easy to grip during opening and closing of the vial. These striations (320) are shown on in FIG. 3A.

Figure 4:
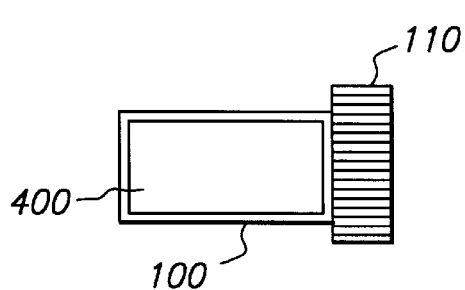
FIG. 4 is an illustration showing one embodiment of the vial of the present invention, upon which a labelling area is included on the exterior of the vial.

In FIG. 4, one preferred embodiment of the vial is shown. In this embodiment, the exterior of the vial (410) is equipped with an labelling area (400) in which identifying information about the dried microorganisms located within the vial. For example, this area allows for the inscription of the name (i.e., genus and species) of the organisms, their accession number (e.g., the number assigned to the particular culture by the ATCC), the date of preservation, etc. This labelling area (400) is intended to provide convenience to both the operator preserving the culture, as well as identify the culture for the operator who revives the culture. It is not intended that the labelling area comprise any particular size. The labelling area may be large or small, depending upon the amount of information needed to be included on the vial. In addition, the labelling area may be an etched region on the outside of the plastic, or it may be an area to which a label may be taped or adhered (e.g., an adhesive label with the identifying information present may be adhered to the vial).

FIGS. 5–8 provide illustrations of the preferred embodiment of the vial and cap combination of the present invention.

Figure 5:
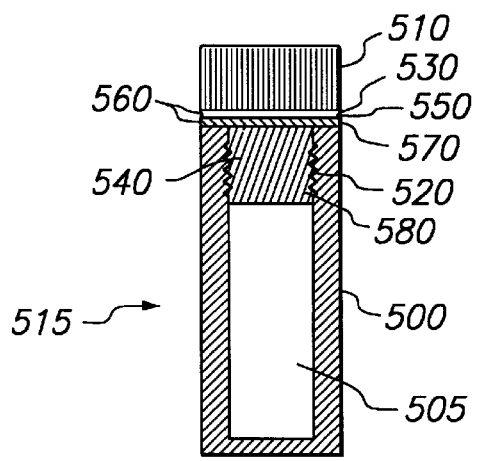
FIG. 5 is a side cross-sectional illustration of one preferred embodiment the vial and cap combination of the present invention.

As shown in FIG. 5, the underside of one embodiment of the cap (510) includes about its periphery, a rim (530), with exterior threads (540) for engagement with the interior threads of (520) of the vial (500). The underside of the cap (510) is further characterized by a circular lip (550). Lip (550), together with rim (530) define a groove (560) for receiving an elastomeric or plastic O-ring, washer, or other sealing device (570) for cooperation with the end of the vial (500) to ensure sealing engagement between the vial (500) and cap (510). The interior (590) of the cap (510) contains an immobilized desiccant (e.g., a desiccant tablet) (580).

Figure 6:
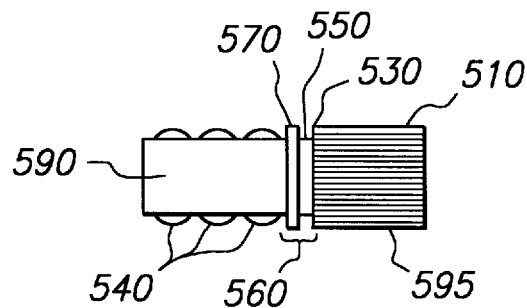
FIG. 6 is a side view of the cap of FIG. 5, showing the placement of the sealing device on the cap structure.
Figure 7:
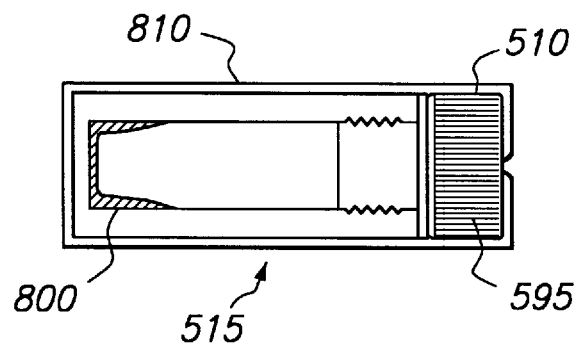
FIG. 7 is an elevational illustration showing the vial and cap combination of one embodiment of the present invention, in which dried organisms are located within the vial and the vial and cap are disposed in a sheath.

In FIG. 7, a side view of one embodiment of the cap, without the vial, is shown. In this Figure, the groove (560) is more easily viewed than in FIG. 5. This Figure shows the a rim (530), with exterior threads (540) for engagement with the interior threads of (520) of the vial (500). As shown in this Figure, Lip (550), together with rim (530) define a groove (560) for receiving an elastomeric or plastic O-ring, washer, or other sealing device (570) for cooperation with the end of the vial (500) to ensure sealing engagement between the vial (500) and cap (510). The interior (590) of the cap (510) may contain an immobilized desiccant (e.g., a desiccant tablet), that is not shown in this Figure. As also shown in FIGS. 5 and 6, the top of the cap (510) that is exposed when the cap (510) and vial (500) are sealingly engaged may have exterior striations (595), which provide advantages in ease of use.

The interior (505) of the sealed vial (500) and cap (510) combination (515) is provided with a dry biologically inert atmosphere. In some embodiments, the atmosphere is oxygen-free. This atmosphere aids in preservation of viable, dried organisms. Those skilled in the art are aware of many methods for producing such an atmosphere, including the use of vacuum. The desiccant (580) present in the cap (510) also assists in maintaining a suitable atmosphere within the interior of the vial.

Figure 8:
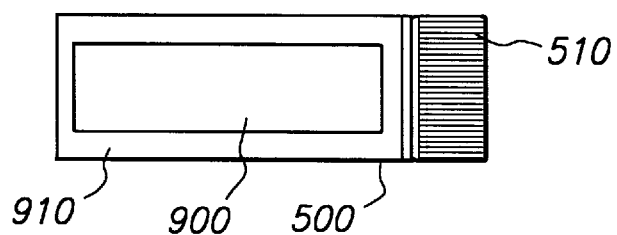
FIG. 8 is an illustration showing one embodiment of the vial of the present invention, upon which a labelling area is included on the exterior of the vial.

In a preferred embodiment, illustrated in FIG. 8, the sealed vial (500) and cap (510) combination (515) contains a film (800) of dried organisms, is itself sealed within a plastic or mylar sheath (810). As shown in FIGS. 5, and 6, this Figure also shows the striations (595) that are included for convenience and safety during the manipulation of the vial (500) and cap (510) combination, in preferred embodiments, the exterior of the vial is striated, such that it is easy to grip during opening and closing of the vial.

In FIG. 9, the exterior of one particularly preferred embodiment of the vial is shown. In this embodiment, the exterior (910) of the vial (500) is equipped with an labelling area (900) in which identifying information about the dried microorganisms located within the vial. For example, this area allows for the inscription of the name (i.e., genus and species) of the organisms, their accession number (e.g., the number assigned to the particular culture by the ATCC), the date of preservation, etc. This labelling area (900) is intended to provide convenience to both the operator preserving the culture, as well as identify the culture for the operator who revives the culture. It is not intended that the labelling area comprise any particular size. The labelling area may be large or small, depending upon the amount of information needed to be included on the vial. In addition, the labelling area may be an etched region on the outside of the plastic, or it may be an area to which a label may be taped or adhered (e.g., an adhesive label with the identifying information present may be adhered to the vial).

In particular, the present invention avoids the hazards associated with the use of glass ampules and vials. Indeed, the use of plastic, screw-capped vials to store and transport the cultures minimizes the danger of breakage during transport, and does not require the vial to be broken in order to retrieve the culture from the vial. In addition, it is easier to revive and retrieve the cultures from the present invention, as compared to the glass vials or other methods used to store and transport viable cultures. For example, unlike the Preceptrol® cultures provided by the American Type Culture Collection (ATCC), there is no metal cap seal to remove from the top of the rubber-stopped vial prior to opening the vial to revive the culture. The present invention simply requires that the cap be unscrewed from the vial and the rehydrating liquid added to the preserved culture within.

The invention further provides for longer viability (i.e., longer shelf life of the cultures) than other methods commonly used for transport of dried cultures (e.g., cultures dried onto inoculating loops, such as Cultiloops® [available from Carr Scarborough Microbiologicals, Inc., Stone Mountain, Ga.] or cultures dried onto swabs).

In contrast with other devices and methods for preservation of microorganisms in which desiccants are used, such as those described in U.S. Pat. No. 5,155,039 to Chrisope et al., incorporated herein by reference, the present invention does not require the fixing of dried microorganisms to the cap. Furthermore, by immobilizing the desiccant in the cap of the present invention and the lyophilized microorganisms in the vial, there is no need to utilize materials such as cotton plugs to prevent contact of the desiccant with the dried microorganisms. By avoiding the use of separating materials and a desiccant that is loosely placed within the vial, less operator manipulation is necessary with the present invention, as compared to that described in U.S. Pat. No. 5,155,039, herein incorporated by reference. This results in a reduced opportunity for contamination of the culture during revival of the dried microorganisms, as well as reducing the potential contamination of the operator and environment resulting from contact with the cotton plug and/or desiccant removed from the vial.

It is also intended that the device of the present invention be provided with a suitable rehydration or revival medium appropriate for the preserved organisms, as known in the art. In this manner, a kit comprising preserved organisms contained within the vial and cap device, as well as a rehydration medium, is provided by the present invention. It is contemplated that in one embodiment, the rehydration medium will be a broth (i.e., liquid) formulation, such as trypticase soy broth or any other fluid medium known in the art, the only requirement being that the rehydration medium be suitable for the organisms to be revived. This rehydration medium can be stored in a separate vial or other container. The rehydration medium is added to the preserved culture when the organisms are to be revived.

Definitions

To facilitate understanding of the invention, a number of terms are defined below.

As used herein, the terms "lyophilized culture" and "freeze-dried culture" are used interchangeably in reference to a culture of organisms that has been freeze-dried. In the freeze-drying or lyophilization process, water vapor is directly removed from the frozen culture by sublimation. In addition, the terms "preserved culture" and "preserved organisms" refer to lyophilized cultures.

As used herein, the terms "preservation container," "ampule," and "vial" refer to containers suitable for preserving microorganisms. It is intended that various containers will be useful in the present invention, including plastic vials (e.g., polypropylene vials, some of which are supplied with polyethylene closures) commercially available from suppliers such as Fisher. Other containers, including standard laboratory flasks, beakers, etc., are also contemplated as being suitable for use in the present invention. It is also intended that in some embodiments, the preservation container will comprise O-rings, washers, or other structures to facilitate sealing of the container.

As used herein, the terms "engaged vial and cap," "sealed vial and cap," "storage vial," "vial and cap combination" refer to the capped preservation container or vial in which preserved organisms are contained (i.e., the cap is closed over the open end of the vial). It is intended that the storage vials be suitable for storage and transport of preserved organisms. Furthermore, in one preferred embodiment, rehydration of the preserved organisms is conducted within the storage vial.

As used herein, the term "desiccant" refers to any material or compound that is useful for drying. Desiccants, include, but are not limited to compounds such as $CaCl_2$, CaO, NaOH, MgO, $CaSO_4$ (e.g., Drierite™), $H_2SO_4$, silica gel, $Mg(ClO_4)_2$, and $P_2O_5$, commercially available from various sources, including Fisher and Multisorb. In one embodiment of the present invention waxed silica gel tablets were used as the desiccant. However, any desiccant that is capable of providing and retaining 1–3% moisture within the vial and cap combination may be used in the present invention.

As used herein, the term "immobilized desiccant" refers to the placement of desiccant within the cap of the present invention in a manner such that the desiccant is retained within the cap. Thus, the desiccant does not come into contact with the preserved organisms present in the vial.

As used herein, the term "vial engaging means" refers to any means by which the cap of the present invention becomes attached to the vial. It is contemplated that various vial engaging means will find use in the present invention, including, but not limited to, threads.

As used herein, the terms "non-breakable" and "unbreakable" refer to materials that are not broken during routine handling. It is contemplated that the plastics or other materials of the vials and caps of the present invention will be non-breakable, in order to minimize the danger of breakage during transport and storage of the vials. This is of particular importance during the shipment of viable microorganisms, as it is desirable to avoid contamination of the microorganism culture, as well as the environment.

As used herein, the term "sheath" refers to a plastic sheath that may be used to seal the container of the present invention. It is intended that the sheath be comprised of any suitable plastic material that is capable of tightly sealing the device. For example, the wraps used to enclose cigarette packages, as well as shrink wraps (e.g., a mylar shrink wrap) used for items such as computer software and foods, may find use in the present invention. It is also contemplated that the sheath may either completely surround the vial and cap device, it may surround only a portion of the vial and cap device, or it may surround only the area where the cap is threaded into the vial.

As used herein, the term "cryoprotectant" refers to compounds or substances which prevent damage to cells during the lyophilization or freezing process. It is intended that the cryoprotectants of the present invention include any compounds or substances that protect the cells from shearing or other mechanical damage that is possible during the preservation process. It is intended to encompass compounds and substances that prevent damage due to the formation of ice crystals during the freezing process. It is further intended that the term encompass compounds and substances that prevent damage that occurs during the rehydration (i.e., revival) of organisms.

As used herein, the term "lyophilization medium" refers to the medium in which organisms are suspended prior to lyophilization. In one embodiment, it is contemplated that cryoprotectants be included in the lyophilization medium. It is not intended that the lyophilization medium be limited to any particular formulation. Indeed, it is contemplated that various formulations will be successfully used in the present invention. For example, it is contemplated that the medium may contain compounds or enzymes such as oxygen-scavenging (e.g., Oxyrase), or other enzymes, anti-oxidants, and other substances that are suitable for use in lyophilization media. As used herein, the term "lyophilization solution" refers to lyophilization medium within which microorganisms are suspended or contained.

As used herein, the terms "revival" and "rehydration" refer to the process of reviving a preserved culture. While it is not intended that the present invention be limited to this method, rehydration is intended to encompass the addition of liquid or fluid to the preserved culture. The suspension of organisms is then used to inoculate suitable microbiological media. The inoculated media are then incubated under conditions suitable for the growth of the organisms, and colonies of organisms present in the preserved culture observed.

As used herein, the term "viability" refers to the ability of a culture to grow. For example, a "viable culture" is comprised of live organisms that are capable of metabolism and growth, while a "non-viable culture" is comprised of cells that are either dead or sufficiently damaged that they are not capable of good growth (i.e., no or abnormally small visible colonies are present), even under optimal conditions for their growth. It is recognized that in some circumstances, a viable culture is not capable of growing well or at all, on a given medium (e.g., microbiological media) under certain conditions, such that growth is visible to the eye. However, it is contemplated that placing such a culture in or on an appropriate medium (including cell cultures or living organisms, such as chick embryos), and under appropriate conditions, the organisms will be capable of growth.

As used herein, the term "shelf-life" refers to the time period during which a culture remains viable. For example, the present invention provides cultures that have long shelf lives. The preserved cultures maintain their viability for long periods of time, as compared to cultures preserved using other methods (e.g., weeks, months, or even years). The viability of the culture is measured following revival of the preserved organisms.

The term "sample" in the present specification and claims are used in its broadest sense. On the one hand, they are meant to include a specimen or culture (i.e., a "sample of microorganisms"). On the other hand, they are meant to include both biological (e.g., organisms isolated from clinical specimens) and environmental samples (i.e., organisms isolated from the environment, rather than a living host). These terms also refers to swabs and other sampling devices which are commonly used to obtain samples for culture of microorganisms.

Biological samples may be animal, including human, fluid or tissue, food products and ingredients such as dairy items, vegetables, meat and meat by-products, and waste. Environmental samples include environmental material such as surface matter, soil, water, and industrial samples, as well as samples obtained from food and dairy processing instruments, apparatus, equipment, disposable, and non-disposable items. These examples are not to be construed as limiting the sample types applicable to the present invention.

Whether biological or environmental, a sample suspected of containing microorganisms may (or may not) first be subjected to an enrichment means to create a "pure culture" of microorganisms. By "enrichment means" or "enrichment treatment," the present invention contemplates (i) conventional techniques for isolating a particular microorganism of interest away from other microorganisms by means of liquid, solid, semi-solid or any other culture medium and/or technique, and (ii) novel techniques for isolating particular microorganisms away from other microorganisms. It is not intended that the present invention be limited only to one enrichment step or type of enrichment means. For example, it is within the scope of the present invention, following subjecting a sample to a conventional enrichment means, to subject the resultant preparation to further purification such that a pure culture of a strain of a species of interest is produced. This pure culture may then be preserved using the device and methods of the present invention.

As used herein, the term "culture" refers to any sample or specimen which is suspected of containing one or more microorganisms. "Pure cultures" are cultures in which the organisms present are only of one strain of a particular genus and species. This is in contrast to "mixed cultures," which are cultures in which more than one genus and/or species of microorganism are present.

As used herein, the term "organism" is used to refer to any species or type of microorganism, including but not limited to bacteria, and fungi. As used herein, the term fungi, is used in reference to eukaryotic organisms such as the molds and yeasts, including dimorphic fungi.

As used herein, the term "spore" refers to any form of reproductive elements produced asexually (e.g., conidia) or sexually by such organisms as bacteria, fungi, algae, protozoa, etc. It is also used in reference to structures within microorganisms such as members of the genus Bacillus, which provide advantages to the individual cells in terms of survival under harsh environmental conditions. It is not intended that the term be limited to any particular type or location of spores, such as "endospores" or "exospores." Rather, the term is used in the very broadest sense.

As used herein, the terms "microbiological media" and "culture media," and "media" refer to any substrate for the growth and reproduction of microorganisms. "Media" may be used in reference to solid plated media which support the growth of microorganisms. Also included within this definition are semi-solid and liquid microbial growth systems including those that incorporate living host organisms, as well as any type of media.

As used herein, the term "carbon source" is used in reference to any compound which may be utilized as a source of carbon for bacterial growth and/or metabolism. Carbon sources may be in various forms, including, but not limited to polymers, carbohydrates, acids, alcohols, aldehydes, ketones, amino acids, and peptides.

As used herein, the term "nitrogen source" is used in reference to any compound which may be utilized as a source of nitrogen for bacterial growth and/or metabolism. As with carbon sources, nitrogen sources may be in various forms, such as free nitrogen, as well as compounds which contain nitrogen, including but not limited to amino acids, peptones, vitamins, and nitrogenous salts.

As used herein, the term "antimicrobial" is used in reference to any compound which inhibits the growth of, or kills microorganisms. It is intended that the term be used in its broadest sense, and includes, but is not limited to compounds such as antibiotics which are produced naturally or synthetically. It is also intended that the term includes compounds and elements that are useful for inhibiting the growth of, or killing microorganisms. It is further intended that antimicrobials be incorporated into lyophilization and/or rehydration media used in the present invention. In this manner, organisms with undesirable characteristics (e.g., contaminants) may be inhibited or killed prior to or during lyophilization and/or revival of the organisms of interest.

As used herein, the term "inoculating suspension" or "inoculant" is used in reference to a suspension which may be inoculated with organisms to be tested. For example, rehydrated organisms may be inoculated onto fresh growth media to monitor their viability. It is not intended that the term "inoculating suspension" be limited to a particular fluid or liquid substance. It is also contemplated that an inoculating suspension may include a component to which water, saline, or any aqueous material is added. It is contemplated in one embodiment, that the component comprises at least one component useful for the intended microorganism. It is not intended that the present invention be limited to a particular component.

As used herein, the term "kit" is used in reference to a combination of reagents and other materials. It is contemplated that the kit may include reagents such as carbon sources, nitrogen sources, chromogenic substrates, antimicrobials, diluents and other aqueous solutions, microplates, inoculants, microcards, and plated agar media, rehydrating media, lyophilization media, and/or storage vials or other containers. The present invention contemplates other reagents useful for the growth, storage, and revival of preserved cultures. For example, the kit may include reagents for detecting the growth of microorganisms following inoculation of kit components. It is not intended that the term "kit" be limited to a particular combination of reagents and/or other materials.

As used herein, the term "primary isolation" refers to the process of culturing organisms directly from a sample. Thus, primary isolation involves such processes as inoculating an agar plate from a culture swab, urine sample, environmental sample, etc. Primary isolation may be accomplished using solid or semi-solid agar media, or in liquid. As used herein, the term "isolation" refers to any cultivation of organisms, whether it be primary isolation or any subsequent cultivation, including "passage" or "transfer" of stock cultures of organisms for maintenance and/or use.

As used herein, the term "presumptive identification" refers to the preliminary identification of an organism based on a minimal array of characteristics, such as observation of colony characteristics, growth on primary isolation media, gram stain results, etc.

As used herein, the term "definitive identification" is used to refer to the final identification of an organism to the genus and/or species level.

As used herein, the term "non-human animal" refers to any animal other than humans. Such non-human animals include vertebrates such as rodents, non-human primates, ovines, bovines, ruminants, lagomorphs, porcines, caprines, equines, canines, felines, aves, etc.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); ng (nanograms); l or L (liters); ml (milliliters); $\mu$l (microliters); cm (centimeters); mm (millimeters); $\mu$m (micrometers); nm (nanometers); °C. (degrees Centigrade); Fisher (Fisher Scientific, Pittsburgh, Pa.); Sigma (Sigma Chemical Co., St. Louis, Mo.); BBL (Becton Dickinson Microbiology Systems, Cockeysville, Md.); DIFCO or Difco (Difco Laboratories, Detroit, Mich.); Clinical Standards Laboratories (Clinical Standards Laboratories, Inc., Rancho Dominguez, Calif.); Multisorb (Multisorb Technologies, Buffalo, N.Y.); and ATCC (American Type Culture Collection, Rockville, Md.).

The desiccant used in the following examples was silica gel formed into a waxed tablet, commercially available from Multisorb. The dimensions of the tablet were determined such that the tablet was securely immobilized within the cap of the vial of the present invention. In one embodiment, the weight of the tablet was 0.36 g prior to waxing, and 0.42 g after waxing. In this embodiment, the vial was 0.36" in length and had an outer diameter of 0.32". This tablet was specifically manufactured to retain 1–3% moisture in the vial and cap combination of the present invention.

EXAMPLE 1

Lyophilization Preservation of Organisms

In this Example, organisms were preserved in various lyophilization media, with and without the use of a desiccant. In this Example, *Escherichia coli* (ATCC 23745), *Campylobacter jejuni* (ATCC 33291), *Haemophilus influenzae* (ATCC 9006), *Bacteriodes fragilis* (ATCC 23745) and *Neisseria gonorrhoea* (ATCC 34126) were tested in these media, in order to identify the optimal formulation to use for the medium formulation.

These cultures were initially grown using media and growth conditions (i.e., incubation temperatures and atmospheres) suitable for their optimal growth, as known to those in the art. In experiments where freshly grown cultures were not used, the organisms were maintained at 4°–8° C., until their use in these experiments.

Various lyophilization media were tested in these experiments for their suitability in providing lyophilized cultures with long-term viability. The media were prepared and sterilized by filter-sterilization using a 0.45$\mu$ filter. The BSA, sucrose, dextrose, NaCl, $K_2HPO_4$, gelatin, cystine, sodium sulfate, charcoal, sodium ascorbate, ascorbic acid, and charcoal used in various formulae were obtained from Sigma. The gelatin used in all of the formulae that contained gelatin, was comprised of porcine skin (Sigma G-2500). The charcoal used in all of the formulae that contained charcoal was comprised of activated charcoal (Sigma C5260). The agar used in various formulae was obtained from Difco. The sodium thioglycollate and thioglycollate medium used in some of these formulae were obtained from Clinical Standards Laboratories; the fluid medium (i.e., the thioglycollate medium in the ninth formulation) was prepared according to the manufacturer's instructions. The trypticase soy broth used in the eighth formulation was obtained from Difco, and was prepared according to the manufacturer's instructions.

The first formulation tested contained the following ingredients prepared in distilled water (per 100 ml medium): 5 g bovine serum albumin (BSA) fraction V, 10 g sucrose, 0.425 g casein peptone, 0.08 g soy peptone, 0.125 g NaCl, 0.06 g $K_2HPO_4$, and 0.06 g dextrose. The peptones used in this formulation, as well as the other formulations (i.e, formulae 2–9), were obtained from Difco and BBL. There was no difference observed between the performance of these peptone formulations.

The second formulation tested contained the following ingredients prepared in distilled water (per 100 ml medium): 5 g bovine serum albumin fraction V, 10 g sucrose, 0.425 g casein peptone, 0.08 g soy peptone, 0.125 g NaCl, 0.06 g $K_2HPO_4$, 0.06 g dextrose, 1.1 g gelatin, and 0.22 g charcoal.

The third formulation tested contained the following ingredients prepared in distilled water (per 100 ml medium): 5 g bovine serum albumin fraction V, 10 g sucrose, 0.425 g casein peptone, 0.08 g soy peptone, 0.125 NaCl, 0.06 g $K_2HPO_4$, 0.06 g dextrose, 1.1 g gelatin, 0.22 g charcoal, and 0.5 g sodium ascorbate.

The fourth formulation tested contained the following ingredients prepared in distilled water (per 100 ml medium): 5 g bovine serum albumin fraction V, 10 g sucrose, 0.425 g casein peptone, 0.08 g soy peptone, 0.06 g NaCl, 0.06 g $K_2HPO_4$, 0.15 g dextrose, 0.1 g sodium thioglycollate powder (Difco), 0.02 g agar, 0.01 cystine, 0.003 g sodium sulfate, and 0.22 g charcoal.

The fifth formulation tested contained the following ingredients prepared in distilled water (per 100 ml medium): 5 g bovine serum albumin fraction V, 7.5 g dextrose, 0.425 g casein peptone, 0.08 g soy peptone, 0.125 NaCl, 0.06 g $K_2HPO_4$, 0.06 g dextrose, 1.1 g gelatin, 0.22 g charcoal, and 0.5 g sodium ascorbate.

The sixth formulation tested contained the following ingredients prepared in distilled water (per 100 ml medium): 5 g bovine serum albumin fraction V, 7.5 g dextrose, 0.425 g casein peptone, 0.08 g soy peptone, 0.06 g NaCl, 0.06 g $K_2HPO_4$, 0.15 g dextrose, 0.1 g powdered sodium thioglycollate, 0.02 g agar, 0.01 cystine, 0.003 g sodium sulfate, and 0.22 g charcoal.

The seventh formulation tested contained the following ingredients prepared in distilled water (per 100 ml medium): 5 g bovine serum albumin fraction V, 10 g sucrose, 0.425 g casein peptone, 0.08 g soy peptone, 0.125 g NaCl, 0.06 g $K_2HPO_4$, 0.06 g dextrose, and 20 ml trypticase soy broth.

The eighth formulation tested contained the following ingredients prepared in distilled water (per 100 ml medium): 5 g bovine serum albumin fraction V, 10 g sucrose, 0.425 g casein peptone, 0.08 g soy peptone, 0.125 g NaCl, 0.06 g $K_2HPO_4$, 0.06 g dextrose, 20 ml trypticase soy broth, and 0.5 g ascorbic acid.

The ninth formulation tested contained the following ingredients prepared in distilled water (per 100 ml medium): 5 g bovine serum albumin fraction V, 10 g sucrose, 0.425 g casein peptone, 0.08 g soy peptone, 0.125 g NaCl, 0.06 g $K_2HPO_4$, 0.06 g dextrose, 20 ml thioglycollate medium, and 0.5 g ascorbic acid.

As indicated above, cultures of the organisms were grown on suitable media as known in the art, and a suspension of each organism comprising the growth obtained from one or more (up to five) petri plates, depending upon the amount of growth obtained for each organism, was aseptically suspended in the test lyophilization media until the media were milky. For example, for *E. coli,* the growth on one plate was sufficient for testing, while for *C. jejuni,* five plates were required in order to obtain a sufficient number of cells. The suspension of organisms in the lyophilization media were placed in screw-capped vials, the vials were labelled with the organism's name (i.e., genus and species), and lyophilized using a Virtis lyophilizer equipped with a chamber in which vials were held during lyophilization, following the instructions of the manufacturer, for 26 hours. For formulae 1–8, no desiccant was used in the caps of the vials. However, for formula 9, desiccant was used in the caps.

After lyophilization, the cultures were quantitated by colony counts (i.e., suspending the organisms in rehydration fluid and then inoculating plated media using calibrated loops and dilutions of the organism suspensions) as is well-known in the art. Then, the vials were stored at 4°–8° C. for more than one year. Lyophilized organisms present in most of the nine formulae were then tested for their viability at monthly intervals by colony counts, as described above. Each lyophilized organism was revived using trypticase soy broth, and plated onto media suitable for the organism, with *B. fragilis* being placed into thioglycollate. The results indicated that the ninth lyophilization medium formulation, used in combination with the desiccant in the cap provided the best preserved cultures, and had the longest shelf life. Although viability was good for the first through eighth formulae for a short amount of time, at 45 days of storage in a commercial laboratory refrigerator (i.e., 4° C.), significant deterioration was observed. For some organisms, deterioration of the preserved cultures rendered them non-viable. For example, the *C. jejuni* lost viability after 3 months of storage, while *N. gonorrhoea* and *H. influenzae* lost 1–2 logs of cells each month, and then became non-viable, and *E. coli* maintained viability over one year of storage, but lost 2–3 logs during this time. These losses were measured in comparison to the results obtained by culturing samples of each of the preserved organisms directly after lyophilization but before storage.

Not all of the cultures were tested each month because product deterioration or "melt-back" (i.e., moisture had entered the vial, which was absorbed by the lyophilized culture) was observed with some of the formulations, and it was not necessary to rehydrate these cultures, as they were likely to be non-viable. Indeed, melt-back became the indicator of formulation success. In addition, inconsistencies were observed with the first through eighth formulae, with some vials producing only slight growth after revival, while other vials in the same lot had either good growth, or were non-viable.

As it was believed that sucrose may have caused viability problems in some of the media containing sucrose, various carbohydrates and differing concentrations were tried. However, the ninth formulation, used in combination with the desiccant, was found to be successful, despite the presence of sucrose in the lyophilization medium.

EXAMPLE 2

Shrink-Wrapping of Vials

In this Example, organisms were preserved according to the methods described in Example 1, with the additional step of after lyophilization, adding a shrink-wrap plastic wrapper to the produce a sheath on the outside of the vials. This step was tested as it was thought that moisture vapor transmission into the vials contributed to the loss of viability observed with the first through eighth formulae described in Example 1. However, it was observed that this was not as an effective method to prevent loss of viability in cultures that were preserved in the ninth lyophilization medium in the presence of desiccant. Thus, cultures preserved in the ninth formulation and maintained in the presence of desiccant (i.e., desiccant was present in the caps of the vials) during their storage performed the best. However, the shrink-wrap sheath may also be used in conjunction with the ninth lyophilization medium formulation and desiccant.

It is clear that the present invention provides the methods and compositions necessary for the safe, efficient, and economical preservation and storage of microorganisms.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A method of preserving a sample of microorganisms, comprising:
   a) providing:
      i) lyophilization medium, ii) viable microorganisms,
iii) a vial, and
iv) a cap, wherein said cap comprises an immobilized desiccant;
b) exposing said viable microorganisms to said lyophilization medium to produce a lyophilization solution;
c) dispensing said lyophilization solution into said vial; and
d) lyophilizing said lyophilization solution to produce a preserved culture.

2. The method of claim 1, further comprising the step of sealing said cap to said vial to produce a vial and cap combination containing said preserved culture.

3. The method of claim 1, further comprising step of sealing said vial and cap combination with a sheath.

4. The sheath of claim 3, wherein said sheath is plastic.

5. The method of claim 1, wherein said lyophilization medium comprises one or more cryoprotectants.

6. The method of claim 1, wherein said lyophilization medium comprises bovine serum albumin fraction V, sucrose, casein peptone, soy peptone, NaCl, $K_2HPO_4$, dextrose, thioglycollate, and ascorbic acid.

7. The method of claim 1, wherein said microorganisms are bacteria.

8. The method of claim 1, wherein said desiccant is selected from the group consisting of $CaCl_2$, CaO, NaOH, MgO, $CaSO_4$ (e.g., Drierite™), $H_2SO_4$, silica gel, $Mg(ClO_4)_2$, and $P_2O_5$.

9. The method of claim 8 wherein said desiccant comprises silica gel.

10. The method of claim 8, wherein said reviving comprises adding rehydration medium to said preserved culture within said vial and cap combination.

11. A method of preserving a sample of microorganisms, comprising:
a) providing:
i) lyophilization medium comprising one or more cryoprotectants,
ii) microorganisms,
iii) a vial, and
iv) a cap, wherein said cap comprises an immobilized desiccant;
b) exposing said microorganisms to said lyophilization medium to produce a lyophilization solution;
c) dispensing said lyophilization solution into said vial;
d) exposing said lyophilization solution to freeze-drying to produce a preserved culture;
e) sealing said cap to said vial to produce a vial and cap combination containing said preserved culture;
f) opening said vial and cap combination; and
g) reviving said preserved microorganisms.

* * * * *

UNITED STATES PATENT AND TRADEMARK OFFICE
CERTIFICATE OF CORRECTION

PATENT NO. : 5,856,172
DATED : 01/05/99
INVENTOR(S) : James R. Greenwood et al.

It is certified that error appears in the above-identified patent and that said Letters Patent is hereby corrected as shown below:

Title page, item [21], after Appl. No.:, please delete "778,478" and insert -- 08/778,478 --.
In the Abstract, in line 3, after the word "cultures", please insert -- and comprises a vial and cap combination wherein the cap comprises an immobilized desiccant and the vial comprises viable microorganisms lyophilized in a lyophilization medium --.
In Column 13, line 66, please delete "0.36"" and insert -- 0.3" --.

Signed and Sealed this

Twenty-eighth Day of March, 2000

Attest:

Q. TODD DICKINSON

*Attesting Officer*    *Commissioner of Patents and Trademarks*